United States Patent [19]

Jon et al.

[11] Patent Number: 5,968,990

[45] Date of Patent: Oct. 19, 1999

[54] WATER-DILUTABLE, MICROEMULSION CONCENTRATE AND POUR-ON FORMULATIONS THEREOF

[75] Inventors: Domingo I. Jon, New York, N.Y.; Donald I. Prettypaul, Englewood, N.J.; Matthew J. Benning, Highland Lakes, N.J.; Kolazi S. Narayanan, Wayne, N.J.; Robert M. Ianniello, Oak Ridge, N.J.

[73] Assignee: ISP Investments Inc., Wilmington, Del.

[21] Appl. No.: 09/160,120

[22] Filed: Sep. 24, 1998

Related U.S. Application Data

[60] Provisional application No. 60/061,944, Oct. 14, 1997.

[51] Int. Cl.$^6$ ............................. A01N 25/00; A01N 25/02
[52] U.S. Cl. ........................................... 514/788; 514/937
[58] Field of Search ...................... 514/788, 937

[56] References Cited

U.S. PATENT DOCUMENTS

| | | | |
|---|---|---|---|
| 5,300,529 | 4/1994 | Naranayan | 514/788 |
| 5,317,042 | 5/1994 | Naranayan | 514/772 |
| 5,389,688 | 2/1995 | Naranayan | 514/788 |

FOREIGN PATENT DOCUMENTS

| | | | |
|---|---|---|---|
| 124253 | 11/1984 | European Pat. Off. | A01N 25/02 |
| 9531898 | 11/1995 | WIPO | A01N 25/04 |
| 9636225 | 11/1996 | WIPO | A01N 25/04 |

*Primary Examiner*—Jose' G. Dees
*Assistant Examiner*—Sabiha N. Qazi
*Attorney, Agent, or Firm*—Walter Katz; William J. Davis; Marilyn J. Maue

[57] ABSTRACT

A water-dilutable, microemulsion concentrate and pour-on formulations for water-insoluble insecticides such as amitraz is described, which includes a mixture of nonionic emulsifiers of defined amounts and HLB values, and, particularly, including a molecular sieve or a water stabilizer additive to provide a single phase, clear, physically and chemically stable system, without decomposition for an extended period of time.

11 Claims, No Drawings

WATER-DILUTABLE, MICROEMULSION CONCENTRATE AND POUR-ON FORMULATIONS THEREOF

CROSS-REFERENCE TO RELATED PATENT APPLICATION

This application is a continuation-in-part of Provisional application Ser. No. 60/061,944, filed Oct. 14, 1997, by the same inventors as herein.

BACKGROUND OF THE INVENTION

1. Field of the Invention

This invention relates to a water-dilutable, microemulsion concentrate and pour-on formulations thereof, particularly for water-insoluble insecticides such as amitraz.

2. Description of the Prior Art

Many different delivery systems are available to deliver agriculturally active chemicals to an animal or plant site. However, such chemicals which are insoluble in water present a formidable challenge to effective use of such pesticide chemicals. Clearly, such chemicals cannot be readily formulated into an aqueous delivery system for pour-on application to animals or plants.

Accordingly, it is an object of this invention to provide a water-dilutable, microemulsion concentrate and pour-on formulations thereof for water-insoluble insecticides.

A specific object herein is to provide stable aqueous delivery systems for the water-insoluble amitraz insecticide.

SUMMARY OF THE INVENTION

What is described herein is a water-dilutable, microemulsion concentrate and aqueous pour-on and dip formulations for insecticide agriculturally active chemicals. The concentrate comprises by weight:

(a) about 3–25% of a water-insoluble insecticide;
(b) about 35–55% of a primary nonionic emulsifier, preferably having an HLB of about 8–9; and
(c) a secondary emulsifier admixture of
  (i) about 10–40% of a $C_8$–$C_{18}$ alkyl pyrrolidone, optionally 0–20% of N-methylpyrrolidone,
  (ii) about 10–35% of a nonionic emulsifier, preferably having an HLB of about 14–16;

the HLB of the concentrate being about 8–11.

Preferred concentrates have (a) about 8–15%; (b) about 38–50%; (c) (i) about 15–30%; and (c) (ii) about 20–30%, wherein (b) is an ethoxylated (EO) castor oil; (c) (i) is a $C_8$ alkyl pyrrolidone; and (c) (ii) is an ethoxylated sorbitan monooleate, and (a) is amitraz.

Most preferred concentrates have (b) an ethoxylated (15 EO) castor oil; (c) (i) a $C_8$ alkyl pyrrolidone; and (c) (ii) an ethoxylated (20 EO) sorbitan monooleate, wherein (a) is amitraz; (b) has an HLB of 8.6; (c) (i) is 22.6–24.2% of $C_8$ alkyl pyrrolidone; and (c) (ii) has an HLB of 15.0.

The concentrate is substantially anhydrous and shows <10% decomposition when stored over a molecular sieve or in the presence of a stabilizer additive at 52° C. for 2 weeks.

The concentrate preferably includes about 1–14% of the N-methylpyrrolidone.

A water-diluted, pour-on use formulation of the invention comprises the concentrate and water of dilution, which, for a pour-on formulation is diluted with water up to about a 1:200 dilution ratio of concentrate:water, preferably giving a 1% insecticide concentration, and wherein substantially 100% of the insecticide is available upon use.

A formulation of the above concentration which is diluted up to 10,000:1 with water is used as a "dip" formulation.

DETAILED DESCRIPTION OF THE INVENTION

The water-dilutable microemulsion concentrate of the invention has the composition in % by weight shown in Table 1 below:

TABLE 1

| Ingredient | Suitable | Preferred |
| --- | --- | --- |
| (a) Agriculturally active chemical e.g. water-unstable insecticide such as amitraz, optionally with pyrethroid, e.g. deltamethrin | 3–25 / 0–6 | 8–15 / 1–4 |
| (b) Primary Nonionic Emulsifier preferably having HLB of 8–9, e.g. ethoxylated (15 EO) castor oil | 35–55 | 38–50 |
| (c) Secondary Nonionic Emulsifiers | | |
| (i) $C_8$–$C_{18}$ alkyl pyrrolidone, e.g. N-octyl pyrrolidone (HLB 6), | 10–40 | 15–30 |
| (ii) a nonionic emulsifier, preferably having HLB of 14–16, e.g. and ethoxylated (20 EO) sorbitan monooleate | 10–35 | 20–30 |
| (d) Molecular sieve or Stabaxol ® I | 5–20 | 7–15 |
| (e) Rhodafac ® RS 710 (pH buffer for pyrethroid) | 0–5 | 0.5–3 |
| (f) Silwet ® L77 (silicone wetting agent) | 0–7 | 0.5–5 |
| (g) HLB of Concentrate | 8–11 | 10 |
| (h) N-Methylpyrrolidone (NMP) | 0–20 | 1–14 |

Amitraz is a triazapentadiene (substituted aromatic di-imidine) compound with insecticide and acaricidal activity; it is only soluble in water to the extent of 1 mg/liter, and has a hydrolysis half-life of 6 hours in an aqueous buffer of pH 7. Usually it is applied to cattle, pigs, dogs and sheep as a pour-on dip or spray formulation, to control ectoparasites, such as mites, ticks, mange and lice.

The amitraz component of the emulsion concentrate of this invention is clear and stable for at least 21 days at 52° C., preferably when stored in the presence of a molecular sieve or a stabilizer additive such as Stabaxol® I. More particularly, under these conditions, greater than 85% of amitraz was retained at elevated temperatures and for an extended period of time.

Upon dilution with water up to 200 times, the emulsion concentrate of the invention provided effective pour-on use formulations which themselves were stable over an extended period even at elevated temperatures.

The invention will now be described in detail with reference to the following examples.

EXAMPLES

Agsol® Ex 1=N-methylpyrrolidone
Agsol® Ex 8=N-octylpyrrolidone
Alkamuls® CO-15=Castor oil ethoxylate (15 EO) (Rhone Poulenc)
Alkamuls® PSMO-20=Sorbitan monooleate (20 EO) (Rhone Poulenc)

Rhodafac® RS 710=Branched ethoxylated phosphate ester (9.75 EO) (Rhone Poulenc)
Silwet® L77=Heptamethyltrisiloxane (Osi Specialties, Inc.)
Molecular Sieves 4A
Stabaxol® I=2,2',6,6'-tetraisopropyldiphenyl carbodiimide (Rhein Chemie)

Example 1

A water dilutable concentrate with amitraz as the active ingredient was prepared by dissolving 13.9 g of technical grade amitraz (72% a.i.) in 86.1 g of a matrix formulation of 21.5 g of N-octylpyrrolidone sold under the name of Agsol Ex 8, 40.4 g of Alkamuls CO-15, and 24.2 g of Alkamuls PSMO-20. The calculated HLB of this matrix as 9.7. The concentrate was dried using 9 g of molecular sieves 4A. HPLC analysis showed greater than 85% retention of a.i. after storing the sample at 52° C. for 21 days. Without the addition of the molecular sieves 4A, more than 90% of the active degraded when stored under similar conditions. The concentrate was then diluted at 1:5, 1:10, 1:20 and 1:100 with 1000 ppm hard water. The diluted samples remained physically stable and clear when kept at room temperature for 3 days. HPLC analysis of the 1:10 dilution sample showed a retention of active of at least 95% after 4 days at 23° C. The particle size of the diluted samples at 90% population was less than 0.04 microns at 20° C., 0.14 microns at 24° C. and 0.2 microns at 35° C. The particle sizes were reversible with a change in temperature, and related to the cloud point of the nonionic surfactants in the formulation.

Example 2

A water dilutable concentrate with amitraz as the active ingredient was prepared by dissolving 13.9 g of technical grade amitraz (72% a.i.) in 86.1 g of a matrix formulation of 16.2 g of Agsol Ex 8, 43.7 g of Alkamuls CO-15 and 26.2 g of Alkamuls PSMO-20. The calculated HLB of this matrix was 10.1. The concentrate was dried using 9 g of molecular sieve 4A. The concentrate was then diluted at a 1:10 ratio with 1000 ppm hard water. The diluted sample remained physically stable and clear at room temperature for 2 days.

Example 3

A water dilutable concentrate with amitraz as the active ingredient was prepared by dissolving 13.9 g of technical grade amitraz (72% a.i.) in 86.1 g of a matrix formulation of 10.8 g of Agsol Ex 8, 47.1 g of Alkamuls CO-15 and 28.3 g of Alkamuls PSMO-20. The calculated HLB of this matrix was 10.4. The concentrate was dried using 9 g of molecular sieves 4A. The concentrate was then diluted at a 1:10 ratio with 1000 ppm hard water. The diluted sample showed some amitraz precipitate within a day.

Example 4

A water based formulation with amitraz as the active ingredient was prepared by dissolving 1 g of technical grade amitraz (72% a.i.) in 99 g of a matrix formulation consisting of 0.37 g of Agsol Ex 8, 6.0 g of Alkamuls CO-15, 3.6 g of Alkamuls PSMO-20 and 1.5 g of Agsol Ex 1. The calculated HLB of this matrix was 10.8. The concentrate was diluted with 87.5 g of water of hardness of 1000 ppm expressed as $CaCO_3$. The diluted samples remained physically stable and clear at room temperature for 2 days.

Example 5

A water based formulation with amitraz as the active ingredient was prepared by dissolving 1 g of technical grade amitraz (72% a.i.) in 99 g of a matrix formulation of 0.12 g of Agsol Ex 8, 6.1 g of Alkamuls CO-15, 1.8 g of Alkamuls PSMO-20 and 1.5 g of Agsol Ex 1. The calculated HLB of this matrix was 10.9. The concentrate was diluted with 87.5 g of 1000 ppm hard water. The diluted sample remained physically stable and clear at room temperature for 1 day.

Example 6

A water based formulation with amitraz as the active ingredient was prepared by dissolving 1 g of technical grade amitraz (72% a.i.) in 99 g of a matrix formulation of 0.62 g of Agsol Ex 8, 5.9 g of Alkamuls CO-15, 3.5 g of Alkamuls PSMO-20 and 1.5 g of Agsol Ex 1. The calculated HLB of this matrix was 10.7. The concentrate was diluted with 87.5 g of 1000 ppm hard water. The diluted sample remained physically stable and clear at room temperature for 2 days.

Example 7

A water dilutable concentrate with amitraz as the active ingredient was prepared by dissolving 13.9 g of technical grade amitraz (72% a.i.) in 86.1 g of a matrix formulation of 21 g of Agsol Ex 8, 40.2 g of Alkamuls CO-15 and 24.8 g of Alkamuls PSMO-20. The calculated HLB of this matrix was 9.8. The concentrate was dried using 9 g of molecular sieves 4A. The concentrate was diluted at a 1:10 ratio with 1000 ppm hard water. The diluted sample remained physically stable and clear at room temperature for 2 days.

Example 8

A water dilutable concentrate with amitraz and deltamethrin as active ingredients were prepared by dissolving 13.9 g of technical grade amitraz (72% a.i.) and 3 g of deltamethrin in 83.1 g of a matrix formulation of 19.9 g of Agsol Ex 8, 39.0 g of Alkamuls CO-15, 23.4 g of Alkamuls PSMO-20 and 0.83 g Rhodafac RS 710. The concentrate was dried using 10 g of molecular sieves 4A. HPLC analysis showed greater than 78% retention of amitraz and greater than 61% retention of deltamethrin after storing the sample at 52° C. for 20 days. The concentrate was diluted at 1:10 and 1:100 with 1000 ppm hard water. The diluted samples remained physically stable and clear at room temperature for 5 days.

Example 9

A water dilutable concentrate with amitraz as the active ingredient was prepared by dissolving 13.9 g of technical grade amitraz (72% a.i.) in 86.1 g of a matrix formulation of 21 g of Agsol Ex 8, 40 g of Alkamuls CO-15, 24 g of Alkamuls PSMO-20 and 0.86 g Rhodafac RS 710. The concentrate was dried using 10 g of molecular sieves 4A. HPLC analysis showed greater than 73% retention of amitraz after storing the sample at 52° C. for 20 days. The concentrate was diluted at 1:10 with 1000 ppm hard water. The diluted sample remained physically stable and clear at room temperature for 3 days.

Example 10

A water dilutable concentrate with deltamethrin as the active ingredient was prepared by dissolving 0.5 g of deltamethrin in 99.5 g of a matrix formulation of 23.8 g of Agsol Ex 8, 46.7 g of Alkamuls CO-15, 28 g of Alkamuls PSMO-20 and 0.99 g Rhodafac RS 710. The concentrate was diluted at 1:10 and 1:100 with 1000 ppm hard water. The diluted samples remained physically stable and opaque when kept at room temperature for 6 days.

Example 11

A water dilutable concentrate with deltamethrin as the active ingredient was prepared by dissolving 3 g of deltamethrin in 97 g of a matrix formulation of 23 g of Agsol Ex 8, 46 g of Alkamuls CO-15, 27 g of Alkamuls PSMO-20 and 0.97 g Rhodafac RS 710. The concentrate was dried using 10 g of molecular sieves 4A. HPLC analysis showed greater than 93% retention of deltamethrin after storing the sample at 52° C. for 20 days. The concentrate was diluted at 1:10 and 1:100 with 1000 ppm hard water. The diluted samples remained physically stable and slightly hazy when kept at room temperature for 1 day, and only hazy for 6 days at 1:100 dilution.

Example 12

A water dilutable concentrate with deltamethrin as the active ingredient was prepared by dissolving 3 g of deltamethrin in 97 g of a matrix formulation of 24 g of Agsol Ex 8, 46 g of Alkamuls CO-15 and 27.6 g of Alkamuls PSMO-20. The concentrate was dried using 10 g of molecular sieves 4A. HPLC analysis showed greater than 50% retention of deltamethrin after storing the sample at 52° C. for 20 days.

Example 13

A water dilutable concentrate with amitraz as the active ingredient was prepared by dissolving 13.9 g of technical grade amitraz (72% a.i.) in 76.1 g of a matrix formulation of 18.4 g of Agsol Ex 8, 36.1 g of Alkamuls CO-15 and 21.6 g of Alkamuls PSMO-20. 10% Stabaxol was added into the formulation in place of the molecular sieves to stabilize the amitraz. HPLC analysis showed greater than 85% retention of a.i. after storing the sample at 52° C. for 14 days. The concentrate was diluted at 1:10 with 1000 ppm hard water. The diluted sample remained physically stable and clear at room temperature over 12 days. HPLC analysis showed a retention greater than 95% or higher after 11 days storage at room temperature.

Example 14

To Example 13 was added 2% Silwet L77, a silicone wetting agent, to enhance spreading and wetting of the microemulsion formulation. The concentrate was diluted at 1:10 with 1000 ppm hard water. A slightly hazy solution was observed due to the presence of the silicone. The silicone material settled out after 1 day at room temperature, but was easily redispersed with slight shaking.

Example 15

To Example 1 was added 2% Silwet L77. The concentrate was diluted at 1:10 with 1000 ppm hard water. A slightly hazy solution was observed again and the silicone material settled out after 1 day at room temperature. However, it easily redispersed with slight shaking.

While the invention has been described with particular reference to certain embodiments thereof, it will be understood that changes and modifications may be made which are within the skill of the art. Accordingly, it is intended to be bound only by the following claims, in which:

What is claimed is:

1. A water-dilutable microemulsion concentrate comprising, by weight:
   (a) (i) 3–25% of a water-insoluble insecticide which is amitraz,
   (ii) 0–6% of a pyrethroid,
   (b) 35–55% of a primary nonionic emulsifier,
   (c) a mixture of secondary nonionic emulsifiers comprising:
   (i) 10–40% of a $C_8$–$C_{18}$ alkyl pyrrolidone, and 0–20% of N-methylpyrrolidone, and
   (ii) 10–35% of a nonionic emulsifier, and
   (d) 5–20% of a molecular sieve or a water stabilizer additive, wherein the HLB of the concentrate is about 8–11.

2. The concentrate according to claim 1 wherein (a) (i) is 8–15%; (a) (ii) is 1–4%; (b) is 38–50%; (c) (i) is 15–30%; (c) (ii) is 20–30%; (d) is 7–15%; and the HLB of the concentrate is about 10.

3. The concentrate according to claim 1 wherein (a) (ii) is deltamethrin; (b) is ethoxylated (15EO) castor oil; (c) (i) is N-octylpyrrolidone, (c) (ii) is ethoxylated (20EO) sorbitan monooleate; and (d) is a molecular sieve 4A.

4. The concentrate according to claim 1 wherein (b) has an HLB of about 8–9; (c) (i) has an HLB of about 6, and (c) (ii) has an HLB of about 14–16.

5. The concentrate according to claim 1 wherein (d) is the additive 2,2',6,6'-tetraisopropyldiphenyl carbodimmide.

6. The concentrate according to claim 1 which includes up to 5% of a pH buffer or up to 7% of a silicone wetting agent, or both.

7. The concentrate according to claim 1 which is clear and stable for at least 2 weeks at 52° C.

8. The concentrate according to claim 6 which includes 0.5–3% of a pH buffer and 0.5–5% of a silicone wetting agent.

9. An aqueous pour-on formulation comprising the concentrate of claim 1 and dilution water up to a 1:200 ratio of concentrate:water.

10. An aqueous pour-on formulation according to claim 9 which has a use level of about 1% active.

11. A dip formulation according to claim 9 which is diluted with water up to 1:10,000 of the concentrate:water.

* * * * *